United States Patent [19]

Levin

[11] Patent Number: 5,399,761
[45] Date of Patent: Mar. 21, 1995

[54] METHOD FOR THE PREPARATION OF 2-HYDROXYARYLALDOXIMES

[75] Inventor: Daniel Levin, Worsley, United Kingdom

[73] Assignee: Zeneca Limited, London, England

[21] Appl. No.: 108,424

[22] Filed: Aug. 19, 1993

[30] Foreign Application Priority Data

Aug. 20, 1992 [GB] United Kingdom ............... 9217724

[51] Int. Cl.$^6$ ............................................ C07C 249/08
[52] U.S. Cl. ................................. 564/259; 564/262
[58] Field of Search ................... 564/259, 265, 262

[56] References Cited

U.S. PATENT DOCUMENTS

| | | | |
|---|---|---|---|
| 3,808,275 | 4/1974 | Hirose et al. | 260/566 A |
| 4,133,834 | 1/1979 | Pickens | 260/566 A |
| 4,231,967 | 11/1980 | Matsuda et al. | 568/433 |
| 4,323,706 | 4/1982 | Bonfield et al. | 564/253 |
| 4,507,248 | 5/1985 | Mathew et al. | 260/500.5 H |

FOREIGN PATENT DOCUMENTS

| | | |
|---|---|---|
| 077279 | 4/1983 | European Pat. Off. . |
| 106653 | 4/1984 | European Pat. Off. . |
| 529870 | 3/1993 | European Pat. Off. . |
| 2218326 | 3/1974 | France . |
| 1310808 | 3/1973 | United Kingdom . |

*Primary Examiner*—Richard L. Raymond
*Assistant Examiner*—B. Burn
*Attorney, Agent, or Firm*—Cushman Darby & Cushman

[57] ABSTRACT

A method for the preparation of a 2-hydroxyarylaldoxime which comprises reacting hydroxylamine with a 2-hydroxyarylaldehyde, said reaction being performed in the presence of a compound of a metal of Group II, Group III, Group IVA or Group VIA of the Periodic Table and/or under such conditions that the 2-hydroxyarylaldehyde is at least partially in the form of a salt and/or complex of a metal of Group II, Group III, Group IVA or Group VIA of the Periodic Table.

29 Claims, No Drawings

METHOD FOR THE PREPARATION OF 2-HYDROXYARYLALDOXIMES

This invention relates to a chemical process and more particularly to a method for the preparation of 2-hydroxyarylaldoximes.

The use of 2-hydroxyarylaldoximes (salicylaldoximes) as extractants in the hydrometallurgical recovery of metals from metal ores is well known. The process is described, for example, in GB-A-1421766 and has been practised commercially for a number of years.

The 2-hydroxyarylaldoximes may be obtained in conventional manner by reacting the corresponding 2-hydroxyarylaldehyde with hydroxylamine. In practice, the hydroxylamine is usually employed in the form of a salt, for example hydroxylammonium sulphate or chloride, and the reaction is performed in the presence of an acid-binding agent such as sodium carbonate which reacts with the liberated acid forming sodium sulphate or chloride, which has to be disposed of, and carbon dioxide. Since the reaction is commonly carried out in a two-phase aqueous and organic solvent medium, the evolution of carbon dioxide can cause loss of organic solvent with economic and environmental consequences unless appropriate and often expensive precautions are taken.

It has now been found that the problems associated with current processes for the preparation of 2-hydroxyarylaldoximes may be obviated or minimised if the 2-hydroxyarylaldehyde is used, at least partially, in the form of a salt and/or complex of certain metals as hereinafter described or in the presence of a compound of said metals. In some cases, a much faster reaction occurs than is the case in the conventional process described above and, furthermore, integration of the oximation reaction with a formylation reaction for preparing the aldehyde allows additional operational savings.

Accordingly, the present invention provides a method for the preparation of a 2-hydroxyarylaldoxime which comprises reacting hydroxylamine with a 2-hydroxyarylaldehyde, said reaction being performed in the presence of a compound of a metal of Group II, Group III, Group IVA or Group VIA of the Periodic Table and/or under such conditions that the 2-hydroxyarylaldehyde is at least partially in the form of a salt and/or complex of a metal of Group II, Group III, Group IVA or Group VIA of the Periodic Table.

As examples of 2-hydroxyarylaldehydes which may be used in the method of the invention, there may be mentioned compounds of the formula:

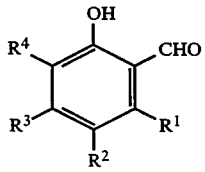

(1)

wherein each of $R^1$, $R^2$, $R^3$ and $R^4$, independently, represents a hydrogen or halogen atom or an alkyl, cycloalkyl, aralkyl, aryl, alkaryl, alkoxy, aryloxy, acyl or hydroxy group. Each of the various hydrocarbyl, hydrocarbyloxy and acyl groups which may be represented by $R^1$, $R^2$, $R^3$ and $R^4$, suitably contains up to 36 carbon atoms, for example from 5 to 22 carbon atoms.

Particular mention may be made of 2-hydroxyarylaldehydes of the formula:

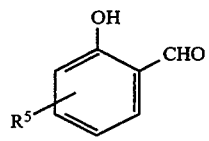

(2)

wherein $R^5$ represents hydrogen or a $C_{1-22}$-alkyl radical, said compounds being used in the preparation of 2-hydroxyarylaldoximes of the formula:

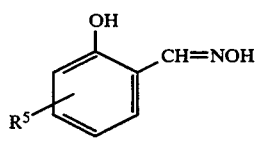

(3)

Preferably, $R^5$ is a $C_{7-12}$-alkyl radical, especially in the 4-position relative to the hydroxyl group.

Because of the presence of the compound of a metal of Group II, Group III, Group IVA or Group VIA of the Periodic Table, it is believed that the 2-hydroxyarylaldehyde will be present in the reaction mixture, at least partially, in the form of a salt, that is to say an aryloxide, and/or a complex of said metal. As examples of particularly suitable metals, there may be mentioned magnesium (Group IIA), aluminium (Group IIIB), titanium and zirconium (Group IVA), and chromium (Group VIA). A metal salt and/or complex of the hydroxyarylaldehyde may be pre-formed or may be generated in the reaction mixture, perhaps only transiently and possibly in equilibrium with one or more other derivatives of the metal.

Reaction conditions suitable for the preparation of 2-hydroxyarylaldehydes in the form of magnesium salts have been described in our EP-A-0529870. Conditions under which 2-hydroxyarylaldehydes may be prepared in the presence of compounds of aluminium, titanium, zirconium and chromium have been described in EP-A-0077279, EP-A-0106653 and U.S. Pat. No. 4,231,967 and these conditions may be expected to lead to the formation of the 2-hydroxyarylaldehyde, at least partially, in the form of salts and/or complexes of said metals.

In performing the method of the invention, the hydroxylamine may advantageously be used in the form of a salt, for example an aqueous solution of a salt. Suitable salts include hydroxylammonium bromide, phosphate, nitrate and acetate but especially the sulphate.

When the hydroxylamine is employed in the form of a salt and the hydroxyarylaldehyde is used in partial salt form, the metal compound being present in less than a chemically equivalent amount relative to the hydroxyarylaldehyde, for example a catalytic amount of a titanium compound, it will usually be necessary to perform the reaction in the presence of a base. Suitable bases include alkali metal hydroxides, carbonates, acetates and the like and nitrogenous bases. When the metal, for example magnesium, is used in at least a chemically equivalent amount relative to the hydroxyarylaldehyde, the addition of a further base as acid-binding agent is not usually necessary.

The reaction upon which the method of the invention is based may be conveniently performed in a suitable solvent medium at temperatures of from 30° to 150° C.

although somewhat lower or higher temperatures may be employed if desired. Suitable solvent media include organic solvents such as alcohols in which both the hydroxyarylaldehyde and the hydroxylamine are soluble to a significant extent. It is preferred, however, to employ the hydroxylamine or salt thereof in the form of an aqueous solution. The hydroxyaldehyde, being at least partially in the form of a salt and/or complex of the metal, may, depending upon its structure and also upon the degree of ionisation, be used as such or in the form of a solution or dispersion in water or in a water-miscible or water-immiscible organic solvent. Preferred solvent systems include mixtures of water and an aromatic hydrocarbon such as toluene or xylene.

The 2-hydroxyarylaldoxime reaction product may be recovered from the reaction mixture in which it is prepared in any conventional manner.

The method of the invention is of particular value for the preparation of 2-hydroxyarylaldoximes by reacting hydroxylamine or a salt thereof with a magnesium salt (bis-aryloxide) of a 2-hydroxyarylaldehyde, especially a 2-hydroxyarylaldehyde of Formula 1 or Formula 2 above and especially for the preparation of the metal extractant 5-nonylsalicylaldoxime from the corresponding magnesium bis-(2-formyl-4-nonylphenoxide).

The method of the invention is also valuable for the preparation of 2-hydroxyarylaldoximes by reacting hydroxylamine or a salt thereof with a 2-hydroxyarylaldehyde, especially a 2-hydroxyarylaldehyde of Formula 1 or Formula 2 above, in the presence of a titanium (IV) derivative. Suitable titanium (IV) derivatives include compounds of the formula:

(4)

wherein each of W, X, Y and Z, independently, represents a halogen atom or an alkoxy, aryloxy, alkaryloxy, aralkoxy, acyloxy or cyclopentadienyl group or a residue of a β-diketone, a hydroxyquinoline or an optionally substituted 2-hydroxybenzaldehyde, or two of W, X, Y and Z together represent an oxygen atom, each of the remaining two, independently, representing a halogen atom or an alkoxy, aryloxy, aralkoxy, alkaryloxy or acyloxy group or a residue of a β-diketone, a hydroxyquinoline or an optionally substituted 2-hydroxybenzaldehyde. Generally, the alkyl or acyl part of a group W, X, Y or Z will contain up to 22 carbon atoms and the aryl part will be phenyl.

Specific examples of titanium (IV) derivatives include titanium tetraisopropoxide, titanium tetrabutoxide and titanium tetraphenoxide.

Methods for the preparation of 2-hydroxyarylaldehydes by the ortho-formylation of optionally substituted phenols in the presence of various metal derivatives have been described in the aforementioned references. In accordance with these methods, 2-hydroxyarylaldehydes are believed to be obtained at least partially in the form of metal salts and/or complexes from with the aldehyde itself may be recovered by conventional techniques, for example by acidification and extraction. It is a particularly advantageous feature of the present invention that the 2-hydroxyarylaldehydes obtained in said formylation processes may be used directly as starting materials without needing to isolate them from the reaction mixtures containing the metal derivatives.

Accordingly, a further aspect of the present invention provides a method for the preparation of a 2-hydroxyarylaldoxime which comprises reacting hydroxylamine with a 2-hydroxyarylaldehyde which is the direct product of reacting a phenol having at least one free ortho position with formaldehyde or a formaldehyde-liberating compound under substantially anhydrous conditions in the presence of a compound of a metal of Group II, Group III, Group IVA or Group VIA of the Periodic Table.

In a preferred embodiment of this aspect of the invention, hydroxylamine or a hydroxylamine salt is reacted with a magnesium 2-formylphenoxide obtained by reacting a magnesium bis-hydrocarbyloxide derived at least in part from a hydroxyaromatic compound having at least one free position ortho to the hydroxyl group with formaldehyde or a formaldehyde liberating compound under substantially anhydrous conditions.

In an especially preferred embodiment of this aspect of the invention, hydroxylamine or a hydroxylamine salt is reacted with a magnesium bis(2-formylphenoxide) obtained by reacting a magnesium bis-phenoxide derived from a phenol having at least one free ortho position with formaldehyde or a formaldehyde-liberating compound under substantially anhydrous conditions.

The substantially anhydrous conditions required by the formylation reaction for production of the magnesium bis(2-formylphenoxide) may be conveniently provided by the use of substantially anhydrous reactants together with conventional techniques, for example distillation, for removal of adventitious moisture. It is usually advantageous to perform the reaction in the presence of a substantially anhydrous solvent system. Suitable solvent systems typically comprise an inert non-polar or low polarity organic solvent and/or a polar organic solvent capable of acting as a ligand with respect to magnesium atoms.

Suitable inert non-polar or low polarity organic solvents will be liquids at the reaction temperature and will act as solvents for the magnesium bis-hydrocarbyloxide. Preferably, they will allow removal of one or more of the volatile by-products by distillation. Examples of suitable inert solvents include aromatic hydrocarbons, for example toluene, xylene, mesitylene, cumene, cymene, tetralin and chlorinated aromatic hydrocarbons, for example chlorobenzene and o-dichlorobenzene. Mixtures of inert solvents may be used.

Suitable polar solvents will be liquids at the reaction temperature and may be regarded as co-solvents when used in conjunction with non-polar or low polarity solvents. As examples of suitable polar co-solvents, there may be mentioned polar aprotic solvents such as dimethylsulphoxide, sulpholane, dimethylacetamide, N-formylpiperidine, N-methylpyrrolidinone, tetramethylurea and, especially, dimethylformamide, tertiary bases such as triethylamine, tri-octylamine, tetramethylethylenediamine and pyridine, ethers such as diethyl ether, diphenyl ether, tetrahydrofuran, glyme, diglyme, triglyme, tris[2-(2-methoxyethoxy)ethyl]amine and crown ethers and other polar solvents such as "Polymeg" 1000 and "Cellosolve" and the like. Particularly useful co-solvents include lower alkanols such as ethanol and, especially, methanol. Mixtures of co-solvents may be used. The co-solvent may be incorporated into the reaction mixture as such or in the form of a ligand already complexed with the magnesium atoms of the bis-aryloxide.

Some solvent materials may have the ability to function as both "solvent" and "co-solvent" in the method of the invention. Thus, for example, a material such as tetrahydrofuran may be used as a solvent in conjunction with a higher polarity co-solvent or as a co-solvent in conjunction with a lower polarity solvent or it may be used as the sole solvent/co-solvent.

The formylation reaction used to prepare the magnesium bis-(2-formylphenoxide) is suitably performed at a reflux temperature within the range from about 60° to about 130° C., by-products of the reaction, for example methanol, methyl formate and methylal, preferably being removed from the reaction mixture as they are formed. The reflux temperature, in any particular case, will depend upon the constitution of the solvent system and upon the pressure being exerted on the reaction zone. Formylation may be satisfactorily performed at atmospheric or higher pressures but, in some cases, it is preferred to carry out the formylation at reduced pressures, that is to say at pressures lower than normal atmospheric pressure, for example at pressures of from 50 to 700 mm Hg (absolute). In particular, it has been found that, in addition to facilitating removal of volatile reaction by-products, a significant improvement in the yield and/or purity of aldehyde and an appreciable reduction in formation of by-products are observed when the reaction is carried out at reduced pressure (and consequently at a lower temperature) compared with carrying out the same reaction in the same solvent system at atmospheric pressure.

In some cases, it may be preferable to carry out the reaction at a reflux temperature in the range from about 70° to about 80° C., for example about 75° C., the reaction pressure being selected to maintain distillation of reaction by-products. Pressures in the range from about 50 to about 500 mm Hg (absolute) will generally provide the preferred reflux temperatures.

Magnesium bis-hydrocarbyloxides which may be used in the formylation reaction are compounds containing two hydrocarbyloxy residues per magnesium atom, at least one of said hydrocarbyloxy residues being aryloxy, for example phenoxy or naphthyloxy, having at least one free position ortho to the oxygen atom. Especially suitable are magnesium bis-phenoxides wherein the phenoxide residues may be unsubstituted or may be substituted in any or all of the positions, other than both the 2- and 6-positions, by substituents which do not interfere with the course of the reaction and which preferably are electron-donating or weakly electron-withdrawing.

Especially useful magnesium bis-phenoxides are derivatives of phenols of the fomula:

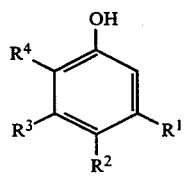

(5)

wherein each of $R^1$, $R^2$, $R^3$ and $R^4$ have the meanings given above.

Particular mention may be made of magnesium bis-phenoxides derived from phenols of the formula:

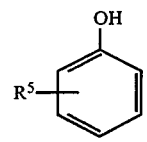

(6)

wherein $R^5$ is as defined above.

The magnesium bis-phenoxides derived from phenols of Formula 5 or Formula 6 may be regarded as compositions containing structures of Formula 7 or Formula 8 respectively as well as related but more complex structures containing more than one magnesium atom per molecule.

In structures of Formula 7:

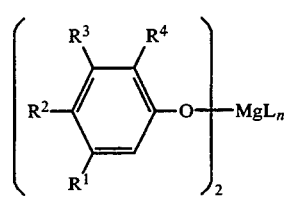

(7)

each of $R^1$, $R^2$, $R^3$ and $R^4$ is as defined above, L represents a ligand molecule derived from another component of the reaction mixture and n represents an integer from 1 to 6.

In structures of Formula 8:

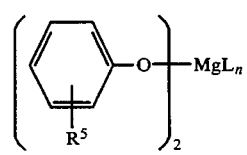

(8)

$R^5$, L and n are as defined above.

Components of the formylation reaction mixture which may provide the ligand molecules L include the co-solvent, formaldehyde and the methanol by-product and mixtures thereof.

It is particularly convenient, however, to use a magnesium bis-aryloxide which, because of its method of preparation, already contains appropriate ligand molecules.

Thus, it is preferred to use a magnesium bis-hydrocarbyloxide which has been prepared by the method described by Ramirez et al in Synthesis, 1979, 71, that is to say by reacting a magnesium alkoxide of the formula:

$$Mg(OR^6)_2 \qquad (9)$$

wherein $R^6$ represents an alkyl, for example a $C_{1-4}$-alkyl, radical, especially methyl, with up to two moles of a phenol having at least one unsubstituted position adjacent to the phenolic hydroxyl group, for example a phenol of Formula 5 or Formula 6. Preferred ratios are from 0.9 to 2, especially from 1.5 to 2, typically about 1.66, moles of phenol per mole of magnesium alkoxide.

The magnesium bis-aryloxides, when used in the formylation reaction contain two aryloxy residues per magnesium atom and are believed also to contain one or more ligand molecules or groups, for example methanol molecules, such that they correspond or are structurally analogous to formula 7. It is to be understood, however, that the present invention is not based upon any theory as to the precise structure of the magnesium bis-phenoxides and is to be regarded as relating to the use of said bis-phenoxides whether in the form of complexes of Formula 7 or not.

Other magnesium bis-hydrocarbyloxides which may be used in the method of the invention include compounds containing one aryloxy and one other hydrocarbyloxy, for example alkoxy, residue per magnesium atom. Such bis-hydrocarbyloxides may be obtained, for example, by reacting one mole of a magnesium alkoxide of Formula 9 with approximately one mole of a phenol having at least one unsubstituted position adjacent to the phenolic hydroxyl group and may, if desired, be used alone or in admixture with the aforementioned bis-aryloxides.

The formaldehyde used in the method of the invention may be in the form of free gaseous formaldehyde or a solution in an anhydrous solvent or a formaldehyde-liberating compound, that is to say a compound capable of liberating formaldehyde under the conditions employed in the method of the invention. Suitable formaldehyde-liberating compounds include polymeric forms of formaldehyde such as paraformaldehyde. It is preferred to add the formaldehyde or formaldehyde-liberating compound gradually (continuously or discontinuously) to the bis-aryloxide in the solvent system.

The formaldehyde or formaldehyde-liberating compound is generally employed in the method of the invention in an amount of at least two moles, expressed as formaldehyde (HCHO), per mole of phenol present in the bis-hydrocarbyloxide. Preferred ratios are from 2 to 3, typically about 2.75 moles of formaldehyde per mole of phenol in the bis-hydrocarbyloxide. The co-solvent is suitably used in an amount not exceeding 5 moles per mole of bis-hydrocarbyloxide, preferred amounts being in the range from 1 to 2 moles per mole of bis-hydrocarbyloxide. These amounts include any co-solvent already present as ligand in the bis-hydrocarbyloxide. Since methanol is a by-product of the reaction, conversion and yield may be maximised by removing this methanol and any other volatile by-products by distillation during the course of the reaction so as to maintain the co-solvent/bis-phenoxide ratio at the optimum level.

In a further valuable embodiment of the invention, hydroxylamine or a salt thereof may be reacted directly with the aluminium, titanium, zirconium or chromium derivatives of 2-hydroxyarylaldehydes obtained in the formylation reactions described in EP-A-0077279, EP-A-0106653 and U.S. Pat. No. 4,231,967 without the need to isolate the hydroxyaldehydes themselves from the reaction mixtures in which they are formed.

The invention is illustrated but not limited by the following Examples.

EXAMPLE 1

Methanol (224 g) and toluene (98 g) were charged to a 2 liter glass reaction vessel followed by magnesium raspings (2.92 g). An activator solution (10 g) was added to activate the magnesium and the mixture was heated to reflux temperature (65° C.) to achieve magnesium dissolution with evolution of hydrogen gas. The mixture was maintained at reflux temperature for 0.5 hour and then further magnesium was added in four portions (4×2.92 g) over a total period of 1.5 hours, each portion being added once hydrogen evolution from the previous portion had subsided. The mixture was then heated under reflux for a further hour to ensure complete magnesium dissolution, 4-nonylphenol (224 g) was added and the mixture heated under reflux for 1 hour to achieve nonylphenol magnesium salt formation. The activator solution was taken from a composition (1116 g) containing nonylphenol magnesium salt (461 g), magnesium methoxide (17.3 g), toluene (194 g) and methanol (443.7 g).

Toluene (175 g) was added and methanol-toluene azeotrope (292 g) was removed by distillation until the reaction mixture temperature reached 90°–95° C. An agitated slurry of paraformaldehyde (85 g) in toluene (120 g) was added to the resulting toluene solution of the nonylphenol magnesium salt at 90°–95° over 3 hours with removal of toluene and volatile by-product distillates (100 g). On completion of paraformaldehyde addition, the reaction mixture was heated to 95°–100° C. for 1 hour to ensure completion of reaction and the mixture was then cooled to 45°–50° C.

A solution of hydroxylamine sulphate (98.5 g) in water (300 g) was added over 1 hour to the formylation reaction mixture at 45°–50° C. Stirring was continued at that temperature for a further 1.5 hours after which the mixture was allowed to settle and the phases were separated.

An acid wash consisting of water (250 g) and sulphuric acid (16 g) was added to the organic phase and the mixture stirred at 45° C. for 0.5 hour. The mixture was allowed to settle and the organic phase was washed with water (2×125 g) at 50° C. Toluene was then removed from the organic phase by evaporation under reduced pressure to leave crude 5-nonylsalicylaldoxime as a yellow oil (271 g). The oxime was purified by distillation at 180° C./0.55 mm Hg.

EXAMPLE 2

In a 500 ml three necked round bottom flask was placed 65.9 g 5-nonylsalicylaldehyde at 90% strength in 48 ml toluene. To this solution was added 2 ml of titanium tetraisopropoxide. The solution became a reddish-brown colour immediately on addition of the titanium complex. The contents were warmed to 45° C. and a solution of 21.8 g of hydroxylamine sulphate in 35 ml water (pre-warmed to 40°–45° C.) was added over 30 seconds. The reaction mixture was stirred at 300 rpm and a solution of 14.5 g sodium carbonate in 30 ml water was added over 5 minutes. The reaction temperature was maintained at 45° C. after the addition was complete. The organic phase was sampled periodically and analysed by GC for the presence of aldehyde. (6×⅛" column of 2% butanediol succinate on Chromosorb WHP). After two hours, analysis indicated 0.7% aldehyde remaining in solution. After three hours, the level of aldehyde had not changed significantly. The stirring was stopped and the aqueous phase removed. The organic phase was washed with 25 ml 5.6% sulphuric acid at 45° C. The aqueous phase was removed and the organic phase washed twice with 35 ml water to a final pH of 2.6. The toluene was removed by rotary evaporation (2 mm Hg, bath temperature 60° C.) to give 69.3 g red-brown oil. Analysis by Cu loading and titration indicated oxime strength of 86.1%.

EXAMPLE 3

The procedure described in Example 1 was repeated except that the hydroxylamine sulphate was replaced by an equivalent amount of hydroxylamine itself (as a 50% solution in water). Addition of the hydroxylamine solution to the formylation reaction mixture produced a yellow milky suspension which slowly turned white. After 1 hour at 45° C., GC analysis showed the oximation reaction to be complete.

After drowning into aqueous sulphuric acid, the toluene layer was very milky but cleared after being stirred for 3 hours. The toluene layer was separated from the aqueous layer, washed with acid then with water and was filtered. Toluene was removed from the organic phase by rotary evaporation to give 5-nonylsalicylaldoxime (87.9% strength) in 87% yield.

EXAMPLE 4

Into a 250 ml round bottomed three necked flask, fitted with a mechanical stirrer, thermometer, and reflux condenser, were charged magnesium raspings (2.95 g, 0.12 mole), dry methanol (75 ml, 1.85 mole) and dry toluene (25 ml). To this was added an 8% solution of magnesium methoxide in methanol (3 ml, 0.002 mole) and the reaction mixture was then heated to reflux. After several minutes, hydrogen evolution was noted. The mixture was heated under reflux for 1 hour until all of the magnesium had dissolved, giving a cloudy white solution/suspension, with no further hydrogen evolution.

P-dodecylphenol (46.8 g, 0.179 mole) was added and the resulting yellow solution heated under reflux for 1 hour before cooling to room temperature under a drying tube overnight. Toluene (120 ml) was charged and the equipment was rearranged for distillation with fractionation. The mixture was heated to remove the methanol as an azeotrope with toluene until an internal temperature of 102° C. was reached. During the distillation (at approx. 97° C.), the viscosity of the solution visibly increased. The fractionation column was then removed and a slurry of paraformaldehyde (18 g, 0.6 mole) in toluene (40 ml) was added at 100°-105° C. in portions over 1 hour with concurrent distillation of solvent and low boiling by-products (59 ml). The reaction was held at 100°-105° C. for 1 hour before cooling to 55° C. for the oximation reaction.

A solution of hydroxylammonium sulphate (19.7 g, 0.12 mole) in water (70 ml) was prepared at 40°-50° C., then added to the reaction vessel over 30 minutes with rapid agitation. The reaction was continued for 3 hours at 55° C., then cooled to 30°-40° C.

The agitator was stopped and the contents transferred to a separation funnel. The aqueous layer was removed and the green/black organic layer was then transferred back to the reaction vessel. A dilute solution of sulphuric acid (13 g, 0.13 mole) in water (100 ml) was charged to the vessel and agitated for 20 minutes at 50° C. A rapid colour change to yellow occurred in the first minute. After this acid treatment, the contents were again transferred to the separation funnel and the acidic aqueous layer was removed. This was followed by two hot ($\approx 50°$ C.) water washes (2×100 ml). The solvent was removed by rotary evaporation to yield 53.25 g of a pale yellow oil. Some of this oil was then distilled using a Leybold apparatus under the following conditions:

wall temp.=230° C., vacuum=2.0 mmHg, addition rate=8.0 ml min$^{-1}$.

This yielded a very pale yellow oil which was found to be 95.3% strength by $^1$H NMR using benzyl acetate as a standard, to give an error of ±2%. This was then used as a standard in order to analyse the crude product by G.C. The crude product was found to be 89.3% strength, giving a yield of 87.3% ±2% of 5-dodecylsalicylaldoxime.

EXAMPLE 5

In a 1.0 L round bottomed three necked flask, fitted with a mechanical stirrer, thermometer, and reflux condenser, were charged magnesium raspings (5.55 g, 0.228 mole), dry methanol (150 ml, 3.7 mole) and dry toluene (50 ml). To this was added an 8% solution of magnesium methoxide in methanol (5 ml, 0.004 mole) and the reaction mixture was then heated to reflux. After several minutes, hydrogen evolution was noted. The mixture was heated under reflux for 1 hour until all of the magnesium had dissolved, giving a cloudy white solution/suspension, with no further hydrogen evolution.

P-chlorophenol (48.7 g, 0.38 mole) was added and the resulting yellow solution heated under reflux for 1½ hours before cooling to room temperature under a drying tube overnight. Toluene (240 ml) was charged and the equipment was rearranged for distillation with fractionation. The mixture was heated to remove the methanol as an azeotrope with toluene until an internal temperature of 100° C. was reached. During the distillation (at approx. 87° C.), precipitation occurred giving a pale slurry. The reaction was then cooled to 90°-95° C. and the fractionation column removed before starting the addition of a slurry of paraformaldehyde (34.1 g, 1.14 mole) in toluene (80 ml) in portions over 1 hour at 90°-95° C. with concurrent distillation of solvent and low boiling by-products (100 ml). The reaction was held at 90°-95° C. for 1 hour before cooling to 55° C. and conversion of the equipment to reflux for the oximation reaction. A yellow slurry had been formed.

A solution of hydroxylammonium sulphate (37.3 g, 0.227 mole) in water (120 ml) was prepared at 40°-50° C., then added to the reaction vessel over 30 minutes with rapid agitation. The reaction was continued for 4½ hours at 55° C., then cooled to 30°-40° C. A white precipitate had formed in the aqueous layer which dissolved on addition of 0.5% v/v solution of sulphuric acid (200 ml).

The agitator was stopped and the contents transferred to a separation funnel. The aqueous layer was removed and the purple/black organic layer was then transferred back to the reaction vessel. A dilute solution of sulphuric acid (16.6 g, 0.166 mole) in water (250 ml) was charged to the vessel and agitated for 20 minutes at 50° C. A rapid colour change to yellow occurred in the first minute. After this acid treatment, the contents were again transferred to the separation funnel and the acidic aqueous layer was removed. This was followed by two hot ($\approx 50°$ C.) water washes (2×100 ml). The solvent was removed by rotary evaporation to yield 49.6 g of a yellow waxy solid which was found to be 42.8% strength by $^1$H NMR using benzyl acetate as a standard, to give a yield of 32.6% of 5-chlorosalicylaldoxime.

EXAMPLE 6

In a 1.0 L round bottomed three necked flask, fitted with a mechanical stirrer, thermometer, and reflux condenser, were charged magnesium raspings (5.85 g, 0.24 mole), dry methanol (150 ml, 3.7 mole) and dry toluene (50 ml). To this was added an 8% solution of magnesium methoxide in methanol (5 ml, 0.004 mole) and the reaction mixture was then heated to reflux. After several minutes, hydrogen evolution was noted. The mixture was heated under reflux for 1 hour until all of the magnesium had dissolved, giving a cloudy white solution/suspension, with no further hydrogen evolution.

P-methoxyphenol (49.6 g, 0.4 mole) was added and the resulting yellow solution heated under reflux for 2 hours before charging toluene (240 ml) and converting the equipment for distillation with fractionation. Methanol was removed as an azeotrope with toluene until an internal temperature of 100° C. was reached. During the distillation (at approx. 78° C.), precipitation occurred giving a pale slurry. The reaction was then cooled to 90°–95° C. and the fractionation column removed before starting the addition of a slurry of paraformaldehyde (36.0 g, 1.2 mole) in toluene (80 ml) in portions over 1 hour at 90°–95° C. with concurrent distillation of solvent and low boiling by-products (68 ml). The reaction was held at 90°–95° C. for 1 hour before cooling to 55° C. and conversion of the equipment to reflux for the oximation reaction. An orange solution had been formed.

A solution of hydroxylammonium sulphate (39.4 g, 0.24 mole) in water (120 ml) was prepared at 40°–50° C., then added to the reaction vessel over 30 minutes with rapid agitation. The reaction was continued for 4½ hours at 55° C., then cooled to room temperature under nitrogen overnight. A white precipitate had formed in the aqueous layer which dissolved on addition of 0.5% v/v solution of sulphuric acid (200 ml). A brown precipitate had also formed in the organic layer. An attempt to dissolve this was made by addition of toluene (100 ml) and heating to 50° C. but the solid remained.

The agitator was stopped and the contents transferred to a separation funnel. The aqueous layer was removed and the brown crystalline slurry/solution organic layer was then transferred back to the reaction vessel, the solids remaining in the separation funnel being washed into the flask with toluene (80 ml). A dilute solution of sulphuric acid (16.6 g, 0.166 mole) in water (250 ml) was charged to the vessel and agitated for 20 minutes at 50° C. A rapid colour change to yellow occurred in the first minute. After this acid treatment, the contents were again transferred to the separation funnel and precipitation occurred. The cloudy acidic aqueous layer was separated, and the organic solution removed. Dichloromethane was added to dissolve the solids, and then combined with the toluene solution above. The cloudy acidic aqueous layer and the aqueous layer from the reaction mixture were both extracted separately using dichloromethane (200 ml). All of the organic layers were combined and the solvent was removed by rotary evaporation to yield 60.5 g of a yellow waxy solid. This solid was then recrystallised from toluene (250 ml) by heating to <70° C. followed by cooling in an ice bath to 0° C. and filtration of the precipitate. This gave 37.1 g of a pale off white solid which was found to be 90.4% strength by $^1$H NMR using benzyl acetate as a standard. The toluene filtrates were rotary evaporated, giving 24.45 g of a brown oil, which later solidified. This was 26.7% strength by $^1$H NMR using benzyl acetate as a standard to give a total yield of 60% of 5-methoxysalicylaldoxime.

EXAMPLE 7

In a 1.0 L round bottomed three necked flask, fitted with a mechanical stirrer, thermometer, and reflux condenser, were charged magnesium raspings (5.85 g, 0.24 mole), dry methanol (150 ml, 3.7 mole) and dry toluene (50 ml). To this was added an 8% solution of magnesium methoxide in methanol (5 ml, 0.004 mole) and the reaction mixture was then heated to reflux. After several minutes, hydrogen evolution was noted. The mixture was heated under reflux for 1 hour until all of the magnesium had dissolved, giving a cloudy white solution/suspension, with no further hydrogen evolution.

O-cresol (43.2 g, 0.4 mole) was added and the resulting yellow solution heated under reflux for 2 hours before cooling to room temperature under a drying tube overnight. Toluene (240 ml) was added and the equipment was rearranged for distillation with fractionation. Methanol was removed as an azeotrope with toluene until an internal temperature of 97° C. was reached. During the distillation (at approx. 80° C.), precipitation occurred giving a brown slurry. The reaction was then cooled to 90°–95° C. and the fractionation column removed before starting the addition of a slurry of paraformaldehyde (36.0 g, 1.2 mole) in toluene (80 ml) in portions over 1 hour at 90°–95° C. with concurrent distillation of solvent and low boiling by-products (89 ml). The reaction was held at 90°–95° C. for 1 hour before cooling to 55° C. and conversion of the equipment to reflux for the oximation reaction. A yellow slurry had been formed.

A solution of hydroxylammonium sulphate (39.4 g, 0.24 mole) in water (120 ml) was prepared at 40°–50° C., then added to the reaction vessel over 30 minutes with rapid agitation. The reaction was continued for 1½ hours at 55° C. A white precipitate had formed in the aqueous layer which dissolved on addition of 0.5% v/v solution of sulphuric acid (250 ml). The agitator was stopped and the contents transferred to a separation funnel.

The aqueous layer was removed and the green/black organic layer was then transferred back to the reaction vessel. A dilute solution of sulphuric acid (33.12 g, 0.331 mole) in water (250 ml) was charged to the vessel and agitated for 20 minutes at 50° C. A rapid colour change to yellow occurred in the first minute. After this acid treatment, the contents were again transferred to the separation funnel and the acidic aqueous layer was removed. This was followed by two hot ($\approx$50° C.) water washes (2×100 ml). The solvent was removed by rotary evaporation to yield 61.1 g of a yellow solid which was found to be 55.1% strength by $^1$H NMR using benzyl acetate as a standard, to give a yield of 55.7% of 3-methylsalicylaldoxime.

EXAMPLE 8

In a 1.0 L round bottomed three necked flask, fitted with a mechanical stirrer, thermometer, and reflux condenser, were charged magnesium raspings (5.85 g, 0.24 mole), dry methanol (150 ml, 3.7 mole) and dry toluene (50 ml). To this was added an 8% solution of magnesium methoxide in methanol (5 ml, 0.004 mole) and the reaction mixture was then heated to reflux. After several minutes, hydrogen evolution was noted. The mixture was heated under reflux for 1 hour until all of the magnesium had dissolved, giving a cloudy white solution/suspension, with no further hydrogen evolution.

M-cresol (43.2 g, 0.4 mole) was added and the resulting yellow solution heated under reflux for 2 hours before cooling to room temperature under a drying tube overnight. Toluene (240 ml) was added and the equipment was rearranged for distillation with fractionation. Methanol was removed as an azeotrope with toluene until an internal temperature of 97° C. was reached. During the distillation (at approx. 87° C.), precipitation occurred giving a cream coloured slurry. The reaction was then cooled to 95° C. and the fractionation column removed before starting the addition of a slurry of paraformaldehyde (36.0 g, 1.2 mole) in toluene (80 ml) in portions over 1 hour at 95° C. with concurrent distillation of solvent and low boiling by-products (79 ml). The reaction was held at 95° C. for 1 hour before cooling to 55° C. and conversion of the equipment to reflux for the oximation reaction. A yellow slurry had been formed.

A solution of hydroxylammonium sulphate (39.4g, 0.24 mole) in water (120 ml) was prepared at 40°–50° C., then added to the reaction vessel over 30 minutes with rapid agitation. The reaction was continued for 4 hours at 55° C. The agitator was stopped and the contents transferred to a separation funnel.

The aqueous layer was removed and the green/black organic layer was then transferred back to the reaction vessel. A dilute solution of sulphuric acid (33.12 g, 0.331 mole) in water (250 ml) was charged to the vessel and agitated for 20 minutes at 50° C. A rapid colour change to yellow occurred in the first minute. After this acid treatment, the contents were again transferred to the separation funnel and the acidic aqueous layer was removed. This was followed by two hot ($\approx 50°$ C.) water washes (2×250 ml). The solvent was removed by rotary evaporation to yield 60.1 g of a yellow solid which was found to be 61.3% strength by $^1$H NMR using benzyl acetate as a standard, to give a yield of 61.0%.

EXAMPLE 9

In a 1.0 L round bottomed three necked flask, fitted with a mechanical stirrer, thermometer, and reflux condenser, were charged magnesium raspings (5.85 g, 0.24 mole), dry methanol (150 ml, 3.7 mole) and dry toluene (50 ml). To this was added an 8% solution of magnesium methoxide in methanol (5 ml, 0.004 mole) and the reaction mixture was then heated to reflux. After several minutes, hydrogen evolution was noted. The mixture was heated under reflux for 1 hour until all of the magnesium had dissolved, giving a cloudy white solution/suspension, with no further hydrogen evolution.

P-cresol (43.2 g, 0.4 mole) was added and the resulting yellow solution heated under reflux for 2 hours before cooling to room temperature under a drying tube overnight. Toluene (240 ml) was added and the equipment was rearranged for distillation with fractionation. Methanol was removed as an azeotrope with toluene until an internal temperature of 98° C. was reached. During the distillation (at approx. 87° C.), precipitation occurred giving a cream coloured slurry. The reaction was then cooled to 95° C. and the fractionation column removed before starting the addition of a slurry of paraformaldehyde (36.0 g, 1.2 mole) in toluene (80 ml) in portions over 1 hour at 95° C. with concurrent distillation of solvent and low boiling by-products (79 ml). The reaction was held at 95° C. for 1 hour before cooling to 55° C. and conversion of the equipment to reflux for the oximation reaction. A yellow slurry had been formed. (During the formylation reaction a physical loss of $\approx 5\%$ occurred due to frothing with a corresponding loss of yield).

A solution of hydroxylammonium sulphate (39.4 g, 0.24 mole) in water (120 ml) was prepared at 40°–50° C., then added to the reaction vessel over 30 minutes with rapid agitation. The reaction was continued for 1½ hours at 55° C. The agitator was stopped and the contents transferred to a separation funnel.

The aqueous layer was removed and the green/black organic layer was then transferred back to the reaction vessel. A dilute solution of sulphuric acid (33.12 g, 0.331 mole) in water (250 ml) was charged to the vessel and agitated for 20 minutes at 50° C. A rapid colour change to yellow occurred in the first minute. After this acid treatment, the contents were again transferred to the separation funnel and the acidic aqueous layer was removed. This was followed by two hot ($\approx 50°$ C.) water washes (2×125 ml). The solvent was removed by rotary evaporation to yield 57.65 g of a yellow solid which was found to be 77.3% strength by $^1$H NMR using benzyl acetate as a standard, to give a yield of 73.8% of 5-methylsalicylaldoxime.

EXAMPLE 10

In a 1.0 L round bottomed three necked flask, fitted with a mechanical stirrer, thermometer, and reflux condenser, were charged magnesium raspings (5.85 g, 0.24 mole), dry methanol (150 ml, 3.7 mole) and dry toluene (50 ml). To this was added an 8% solution of magnesium methoxide in methanol (5 ml, 0.004 mole) and the reaction mixture was then heated to reflux. After several minutes, hydrogen evolution was noted. The mixture was heated under reflux for 1 hour until all of the magnesium had dissolved, giving a cloudy white solution/suspension, with no further hydrogen evolution.

2,4-dimethylphenol (48.8 g, 0.4 mole) was added and the resulting yellow solution heated under reflux for 2 hours before cooling to room temperature under a drying tube overnight. Toluene (240 ml) was added and the equipment was rearranged for distillation with fractionation. Methanol was removed as an azeotrope with toluene until an internal temperature of 95° C. was reached. During the distillation (at approx. 92° C.), the viscosity of the solution increased. The reaction was then cooled to 93° C. and the fractionation column removed before starting the addition of a slurry of paraformaldehyde (36.0 g, 1.2 mole) in toluene (80 ml) in portions over 1 hour at 95° C. with concurrent distillation of solvent and low boiling by-products (67 ml). The reaction was held at 95° C. for 1½ hours before cooling to 55° C. and conversion of the equipment to reflux for the oximation reaction. A yellow solution had been formed.

A solution of hydroxylammonium sulphate (39.4 g, 0.24 mole) in water (120 ml) was prepared at 40°14 50° C., then added to the reaction vessel over 30 minutes with rapid agitation. The reaction was continued for 1½ hours at 55° C., before cooling to room temperature overnight. A white precipitate had formed in the aqueous layer which dissolved on addition of 0.5% v/v solution of sulphuric acid (200 ml). A pale brown precipitate had also formed in the organic layer. The solid in the organic phase re-dissolved on heating to 50° C.

The agitator was stopped and the contents transferred to a separation funnel. The aqueous layer was removed quickly due to a precipitate forming in the organic layer. The brown crystalline slurry/solution organic layer was then transferred back to the reaction vessel and some of the solids remaining in the separation funnel were washed into the flask with toluene (50 ml). A dilute solution of sulphuric acid (33.12 g, 0.331 mole) in water (250 ml) was charged to the vessel and agitated for 20 minutes at 50° C. A rapid colour change to yellow occurred in the first minute. After this acid treatment, the contents were again transferred to the separation funnel and the acidic aqueous layer was removed. This was followed by two hot ($\approx 65°$ C.) water washes (2×125 ml). The organic layer which had already started to precipitate, was then transferred to a conical flask and placed in an ice bath to complete the precipitation. The solid was then filtered off giving a yield of ≈29 g. The filtrates were then reduced in volume to about half by rotary evaporation giving a second crop which was again filtered off to yield ≈13 g. This procedure was repeated and a third crop was obtained, yield ≈5 g. The solids were combined to give a white solid weighing 47.8 g which was found to be 36.9% strength by $^1$H NMR using benzyl acetate as a standard. The filtrates were then rotary evaporated to dryness giving a yellow solid weighing 18.8 g which was found to be 22.4% strength by $^1$H NMR using benzyl acetate as a standard. This gave a total yield of 32.8% of 3,5-dimethylsalicylaldoxime.

EXAMPLE 11

In a 500 ml round bottomed three necked flask, fitted with a mechanical stirrer, thermometer, and reflux condenser, were charged magnesium raspings (2.92 g, 0.12 mole), dry methanol (80 ml, 2.0 mole) and dry toluene (20 ml). To this was added an 8% solution of magnesium methoxide in methanol (2 ml, 0.0015 mole) and the reaction mixture was then heated to reflux. After several minutes, hydrogen evolution was noted. The mixture was heated under reflux for 1 hour until all of the magnesium had dissolved, giving a cloudy white solution/suspension, with no further hydrogen evolution.

O-sec-butylphenol (30.0 g, 0.2 mole) was added and the resulting yellow solution heated under reflux for 3 hours before cooling to room temperature under a drying tube overnight. Toluene (120 ml) was charged and the equipment was rearranged for distillation with fractionation. The mixture was heated to remove the methanol as an azeotrope with toluene until an internal temperature of 102° C. was reached. During the distillation, the mixture remained a thin stirrable green solution. The reaction was then cooled to 90°–95° C. and the fractionation column removed before starting the addition of a slurry of paraformaldehyde (18.0 g, 0.6 mole) in toluene (40 ml) in portions over 1 hour at 95°–98° C. with concurrent distillation of solvent and low boiling by-products (62 ml). The reaction was held at 99° C. for 40 minutes before cooling to 55° C. and conversion of the equipment to reflux for the oximation reaction. A yellow solution had been formed.

A solution of hydroxylammonium sulphate (19.7 g, 0.12 mole) in water (60 ml) was prepared at 40°–50° C., then added to the reaction vessel over 30 minutes with rapid agitation. The reaction was continued for 2½ hours at 55° C., then cooled to room temperature overnight. A white precipitate had formed in the aqueous layer which dissolved on addition of 0.5% v/v solution of sulphuric acid (200 ml), and heating to 45° C.

The agitator was stopped and the contents transferred to a separation funnel. The aqueous layer was removed and the purple/black organic layer was then transferred back to the reaction vessel. A dilute solution of sulphuric acid (16.6 g, 0.166 mole) in water (100 ml) was charged to the vessel and agitated for 30 minutes at 50° C. A rapid colour change to yellow occurred in the first minute. After this acid treatment, the contents were again transferred to the separation funnel and the acidic aqueous layer was removed. This was followed by two hot (≈50° C.) water washes (2×100 ml). The solvent was removed by rotary evaporation to yield 38.6 g of an orange oil which was found to be 14.4% strength by $^1$H NMR using benzyl acetate as a standard, to give a yield of 14.4% of 3-sec-butylsalicylaldoxime.

EXAMPLE 12

In a 500 ml round bottomed three necked flask, fitted with a mechanical stirrer, thermometer, and reflux condenser, were charged magnesium raspings (1.46 g, 0.06 mole), dry methanol (50 ml, 1.23 mole) and dry toluene (10 ml). To this was added an 8% solution of magnesium methoxide in methanol (1 ml, 0.00074 mole) and the reaction mixture was then heated to reflux. After several minutes, hydrogen evolution was noted. The mixture was heated under reflux for 1 hour until all of the magnesium had dissolved, giving a cloudy white solution/suspension, with no further hydrogen evolution.

M-tert-butylphenol (15.0 g, 0.1 mole) was added and the resulting yellow solution heated under reflux for 1½ hours before cooling to room temperature under a drying tube overnight. Toluene (70 ml) was charged and the equipment was rearranged for distillation with fractionation. The mixture was heated to remove the methanol as an azeotrope with toluene until an internal temperature of 97° C. was reached. During the distillation (at approx. 93° C.), the viscosity of the solution increased. The reaction was then cooled to 95° C. and the fractionation column removed before starting the addition of a slurry of paraformaldehyde (9.0 g, 0.3 mole) in toluene (20 ml) in portions over 50 minutes at 93°–95° C. with concurrent distillation of solvent and low boiling byproducts (34 ml). The reaction was held at 95° C. for 40 minutes before cooling to 55° C. and conversion of the equipment to reflux for the oximation reaction. A yellow slurry had been formed.

A solution of hydroxylammonium sulphate (9.85 g, 0.06 mole) in water (30 ml) was prepared at 40°–50° C., then added to the reaction vessel over 30 minutes with rapid agitation. The reaction was continued for 2 hours at 55° C., then cooled to room temperature overnight. A small amount of white precipitate had formed in the aqueous layer which dissolved on addition of 0.5% v/v solution of sulphuric acid (100 ml), and heating to 50° C.

The agitator was stopped and the contents transferred to a separation funnel. The aqueous layer was removed and the purple/black organic layer was then transferred back to the reaction vessel. A dilute solution of sulphuric acid (11.04 g, 0.11 mole) in water (50 ml) was charged to the vessel and agitated for 20 minutes at 50° C. A rapid colour change to yellow occurred in the first minute. After this acid treatment, the contents were again transferred to the separation funnel and the acidic aqueous layer was removed. This was followed by two hot (≈50° C.) water washes (2×75 ml). The solvent was removed by rotary evaporation to yield 16.7 g of a pale yellow oil, which later solidified. This was found to be 73.0% strength by $^1$H NMR using benzyl acetate as a standard, to give a yield of 63.2%. Only one regioisomer (4-tert-butylsaiicylaldoxime) was detected by G.C. analysis.

EXAMPLE 13

In a 1.0 L round bottomed three necked flask, fitted with a mechanical stirrer, thermometer, and reflux condenser, were charged magnesium raspings (5.85 g, 0.24 mole), dry methanol (150 ml, 3.7 mole) and dry toluene (50 ml). To this was added an 8% solution of magnesium methoxide in methanol (5 ml, 0.004 mole) and the reaction mixture was then heated to reflux. After several minutes, hydrogen evolution was noted. The mixture was heated under reflux for 1 hour until all of the magnesium had dissolved, giving a cloudy white solution/suspension, with no further hydrogen evolution.

Phenol (37.6 g, 0.40 mole) was added and the resulting yellow solution heated under reflux for 45 minutes before cooling to room temperature under a drying tube overnight. Toluene (240 ml) was charged and the equipment was rearranged for distillation with fractionation. The mixture was heated to remove the methanol as an azeotrope with toluene until an internal temperature of 95° C. was reached. During the distillation (at approx. 90° C.), precipitation occurred giving a pale slurry. The reaction was then cooled to 90°-95° C. and the fractionation column removed before starting the addition of a slurry of paraformaldehyde (36.0 g, 1.2 mole) in toluene (80 ml) in portions over 1 hour at 95° C. with concurrent distillation of solvent and low boiling by-products (100 ml). The reaction was held at 90°-95° C. for 1 hour before cooling to 55° C. and conversion of the equipment to reflux for the oximation reaction. A yellow slurry had been formed.

A solution of hydroxylammonium sulphate (37.3 g, 0.227 mole) in water (120 ml) was prepared at 40°-50° C., then added to the reaction vessel over 30 minutes with rapid agitation. The reaction was continued for 2 hours at 55° C., then cooled to 30°-40° C. and the agitator stopped. A poor separation resulted which improved on addition of 1.0% v/v solution of sulphuric acid (100 ml).

The contents of the reaction vessel were then transferred to a separation funnel. The aqueous layer was removed and the purple/black organic layer was then transferred back to the reaction vessel. A dilute solution of sulphuric acid (36.8 g, 0,368 mole) in water (250 ml) was charged to the vessel and agitated for 20 minutes at 50° C. A rapid colour change to yellow occurred in the first minute. After this acid treatment, the contents were again transferred to the separation funnel and the acidic aqueous layer was removed. This was followed by two hot ($\approx 50°$ C.) water washes (2×100 ml). The solvent was removed by rotary evaporation to yield 51.3 g of a yellow oil which later partially solidified, and was found to be 63.0% strength by $^1$H NMR using benzyl acetate as a standard, to give a yield of 59.0% of salicylaldoxime.

EXAMPLE 14

In a 1.0 L round bottomed three necked flask, fitted with a mechanical stirrer, thermometer, and reflux condenser, were charged magnesium raspings (5.85 g, 0.24 mole), dry methanol (150 ml, 3.7 mole) and dry toluene (50 ml). To this was added an 8% solution of magnesium methoxide in methanol (5 ml, 0.004 mole) and the reaction mixture was then heated to reflux. After several minutes, hydrogen evolution was noted. The mixture was heated under reflux for 1 hour until all of the magnesium had dissolved, giving a cloudy white solution/suspension, with no further hydrogen evolution.

α-Naphthol (57.6 g, 0.4 mole) was added and the resulting yellow solution heated under reflux for 1 hour before cooling to room temperature under a drying tube overnight. Toluene (240 ml) was charged and the equipment was rearranged for distillation with fractionation. Methanol was removed as an azeotrope with toluene until an internal temperature of 99° C. was reached. During the distillation, the mixture remained a thin stirrable dark brown solution. The reaction was then cooled to 90°-95° C. and the fractionation column removed before starting the addition of a slurry of paraformaldehyde (36.0 g, 1.2 mole) in toluene (80 ml) in portions over 1½ hours at 95°-99° C. with concurrent distillation of solvent and low boiling by-products (95 ml). The reaction was held at 97° C. for 1½ hours before cooling to 55° C. and conversion of the equipment to reflux for the oximation reaction. A bottle green slurry had been formed.

A solution of hydroxylammonium sulphate (39.4 g, 0.24 mole) in water (120 ml) was prepared at 40°-50° C., then added to the reaction vessel over 30 minutes with rapid agitation. The reaction was continued for 5½ hours at 55° C., then cooled to room temperature overnight. The bottle green precipitate had remained unchanged, but was now predominantly in the aqueous phase. The solid was filtered off from the two phases and dried, to give the crude 1-hydroxynaphthalene-2-carboxaldehyde oxime (magnesium salt) weighing 82.9 g.

EXAMPLE 15

In a 1.0 L round bottomed three necked flask, fitted with a mechanical stirrer, thermometer, and reflux condenser, were charged magnesium raspings (5.85 g, 0.24 mole), dry methanol (150 ml, 3.7 mole) and dry toluene (50 ml). To this was added an 8% solution of magnesium methoxide in methanol (5 ml, 0.004 mole) and the reaction mixture was then heated to reflux. After several minutes, hydrogen evolution was noted. The mixture was heated under reflux for 1 hour until all of the magnesium had dissolved, giving a cloudy white solution/suspension, with no further hydrogen evolution.

β-Naphthol (57.6 g, 0.4 mole) was added and the resulting mixture solidified. Toluene (200 ml) was added giving a thick slurry to which an addition of methanol (50 ml) was made. The slurry was heated under reflux for 1 hour before cooling to room temperature under a drying tube overnight. Toluene (240 ml) was charged and the equipment was rearranged for distillation with fractionation. Methanol was removed as an azeotrope with toluene until an internal temperature of 99° C. was reached. During the distillation, the thick slurry increased in viscosity until the surface of the mixture was not being agitated. The reaction was then cooled to 93°-95° C. and the fractionation column removed before starting the addition of a slurry of paraformaldehyde (36.0 g, 1.2 mole) in toluene (80 ml) in portions over 1½ hours at 95°-99° C. with concurrent distillation of solvent and low boiling by-products (72 ml). The reaction was held at 99° C. for 2 hours, at which point a sample was taken and the reaction was shown to be incomplete. A further addition of paraformaldehyde (20 g, 0.66 mole) as a slurry in toluene (40 ml) was therefore carried out over 25 minutes. The reaction was stirred at 99° C. for a further 2 hours before removal of excess toluene (120 ml) by distillation, followed by cooling to 55° C. and conversion of the equipment to reflux for the oximation reaction. A mustard yellow coloured slurry had been formed.

A solution of hydroxylammonium sulphate (39.4 g, 0.24 mole) in water (120 ml) was prepared at 40°-50° C., then added to the reaction vessel over 30 minutes with rapid agitation. The reaction was continued for 3 hours at 55° C., then cooled to room temperature overnight. The mixture had turned green. A white precipitate had formed in the aqueous layer which dissolved on addition of 0.5% v/v solution of sulphuric acid (200 ml), and heating to 50° C. The agitator was stopped and a poor separation resulted which improved on addition of common salt (25 g).

The contents of the reaction vessel were then transferred to a separation funnel. The aqueous layer was removed and the brown organic layer was then transferred back to the reaction vessel. A dilute solution of sulphuric acid (36.8 g, 0.368 mole) in water (250 ml) was charged to the vessel and agitated for 20 minutes at 50° C. No colour change occurred. The brown solution was then transferred back to the separation funnel and the acidic aqueous layer was removed. This was followed by two hot ($\approx 50°$ C.) water washes (2×100 ml). The solvent was removed by rotary evaporation to yield 70.4 g of crude 2-hydroxynaphthalene-1-carboxaldehyde oxime.

EXAMPLE 16

Into a 1 L round bottomed three necked flask, fitted with a mechanical stirrer, thermometer, and reflux condenser, were charged magnesium raspings (14.6 g, 0.6 mole), dry methanol (284 ml, 7.0 mole) and dry toluene (112 ml). To this was added an 8% solution of magnesium methoxide in methanol (5 ml, 0.004 mole) and the reaction mixture was then heated to reflux. After several minutes, hydrogen evolution was noted. The reaction was heated under reflux for 1½ hours until all of the magnesium had dissolved, giving a cloudy white solution/suspension, with no further hydrogen evolution.

P-nonylphenol (220.0 g, 1.0 mole) was added and the resulting yellow solution heated under reflux for 1 hour before cooling to room temperature under a drying tube overnight. Toluene (240 ml) was charged and the equipment was rearranged for distillation with fractionation under vacuum. The mixture was heated to remove the methanol as an azeotrope with toluene at a pressure of 380 mmHg, until an internal temperature of 75° C. was reached. During the distillation (at approx. 71° C.), the viscosity of the solution visibly increased. A slurry of paraformaldehyde (90 g, 3.0 mole) in toluene (150 ml) was then added at 75°–77° C. in portions over 2 hours with concurrent distillation of solvent and low boiling by-products (210 ml). The internal reaction temperature was maintained at 75°–77° C. by means of a gradual reduction in pressure to 270 mmHg throughout the addition. The reaction was held at 75° C./270 mmHg for 1 hour before releasing the vacuum, rearranging the equipment for reflux and cooling to 55° C. for the oximation reaction.

A solution of hydroxylammonium sulphate (98.5 g, 0.6 mole) in water (300 ml) was prepared at 40°–50° C., then added to the reaction vessel over 30 minutes with rapid agitation. The reaction was continued for 3 hours at 55° C., then cooled to 30°–40° C.

The agitator was stopped and the contents transferred to a separation funnel. The aqueous layer was removed and the purple/black organic layer was then transferred back to the reaction vessel. A dilute solution of sulphuric acid (18.4 g, 0.184 mole) in water (250 ml) was charged to the vessel and agitated for 20 minutes at 50° C. A rapid colour change to yellow occurred in the first minute. After this acid treatment, the contents were again transferred to the separation funnel and the acidic aqueous layer was removed. This was followed by two hot ($\approx 50°$ C.) water washes (2×250 ml). The solvent was removed by rotary evaporation to yield 261.8 g of a pale yellow oil which was found to be 87.0% strength by G.C., giving a yield of 86.6% of 5-nonylsalicylaldoxime.

EXAMPLE 17

In a 1.0 L round bottomed three necked flask, fitted with a mechanical stirrer, thermometer, and reflux condenser, were charged magnesium raspings (5.85 g, 0.24 mole), dry methanol (150 ml, 3.7 mole) and dry toluene (50 ml). To this was added an 8% solution of magnesium methoxide in methanol (5 ml, 0.004 mole) and the reaction mixture was then heated to reflux. After several minutes, hydrogen evolution was noted. The mixture was heated under reflux for 1 hour until all of the magnesium had dissolved, giving a cloudy white solution/suspension, with no further hydrogen evolution.

P-methoxyphenol (48.6 g, 0.39 mole) was added and the resulting yellow solution heated under reflux for 1 hour before cooling to room temperature under a drying tube overnight. Toluene (240 ml) was charged and the equipment was rearranged for distillation with fractionation under vacuum. The mixture was heated to remove the methanol as an azeotrope with toluene at a pressure of 380 mmHg, until an internal temperature of 75° C. was reached. During the distillation (at approx. 64° C.), a precipitation occurred giving a pale slurry. A slurry of paraformaldehyde (36 g, 1.2 mole) in toluene (80 ml) was then added at 75°–77° C. in portions over 1½ hours with concurrent distillation of solvent and low boiling by-products (63 ml). The internal reaction temperature was maintained at 75°–77° C. by means of a gradual reduction in pressure to 270 mmHg throughout the addition. The reaction was held at 75° C./270 mmHg for 1 hour before releasing the vacuum, rearranging the equipment for reflux and cooling to 55° C. for the oximation reaction. A solution of hydroxylammonium sulphate (39.4 g, 0.24 mole) in water (120 ml) was prepared at 40°–50° C., then added to the reaction vessel over 30 minutes with rapid agitation. The reaction was continued for 3 hours at 55° C., then cooled to room temperature under nitrogen overnight. A brown precipitate had formed in the aqueous layer.

The solid was filtered off from the two phases and the filtrates were then transferred to a separation funnel. The aqueous layer was removed. The solid filter cake and the organic layer were then transferred back to the reaction vessel and a dilute solution of sulphuric acid (36.8 g, 0.368 mole) in water (250 ml) was charged and then agitated for 20 minutes at 50° C. A rapid colour change to yellow occurred in the first minute. After this acid treatment, the contents were transferred to the separation funnel. The cloudy acidic aqueous layer was separated quickly, due to a precipitate forming, and the organic solution/suspension was washed with two hot ($\approx 65°$ C.) water washes (2×100 ml). The toluene solution/suspension was then transferred to a conical flask and placed in an ice bath to complete the precipitation. The pale yellow solid (27.9 g) was then filtered off and dried. The cloudy acidic aqueous layer and the aqueous layer from the reaction mixture were both extracted separately using dichloromethane (200 ml). The organic layers were combined (dichloromethane from aqueous extracts and the toluene filtrates) and the solvent was removed by rotary evaporation to yield 33.6g of a yellow solid. Both solids were analysed by G.C. using a standard of known strength to give a combined yield of 41% of 5-methoxysalicylaldoxime.

EXAMPLE 18

In a 1.0 L round bottomed three necked flask, fitted with a mechanical stirrer, thermometer, and reflux condenser, were charged magnesium raspings (5.85 g, 0.24 mole), dry methanol (150 ml, 3.7 mole) and dry toluene (50 ml). To this was added an 8% solution of magnesium methoxide in methanol (5 ml, 0.004 mole) and the reaction mixture was then heated to reflux. After several minutes, hydrogen evolution was noted. The mixture was heated under reflux for 1 hour until all of the magnesium had dissolved, giving a cloudy white solution/suspension, with no further hydrogen evolution.

2,4-Dimethylphenol (48.8 g, 0.4 mole) was added and the resulting yellow solution heated under reflux for 1½ hours before cooling to room temperature under a drying tube overnight. Toluene (240 ml) was added and the equipment was rearranged for distillation with fractionation under vacuum. The mixture was heated to remove the methanol as an azeotrope with toluene at a reduced pressure of 380 mmHg, until an internal temperature of 75° C. was reached. During the distillation (at approx. 71° C.), the viscosity of the solution visibly increased. A slurry of paraformaldehyde (36.0 g, 1.2 mole) in toluene (80 ml) was added at 75°–77° C. in portions over 2 hours with concurrent distillation of solvent and low boiling by-products (100 ml). The internal reaction temperature was maintained at 75°–77° C. by means of a gradual reduction in pressure to 245 mmHg throughout the addition. The reaction was held at 75° C./245 mmHg for 1 hour before releasing the vacuum, rearranging the equipment for reflux and cooling to 55° C. for the oximation reaction. A yellow solution had been formed.

A solution of hydroxylammonium sulphate (39.4 g, 0.24 mole) in water (120 ml) was prepared at 40°–50° C., then added to the reaction vessel over 30 minutes with rapid agitation. The reaction was continued for 3 hours at 55° C., before cooling to room temperature overnight. A white precipitate had formed in the aqueous layer which dissolved on addition of 0.5% v/v solution of sulphuric acid (200 ml). A pale brown precipitate had also formed in the organic layer. The solid in the organic phase re-dissolved on heating to 50° C.

The agitator was stopped and the contents transferred to a separation funnel. The aqueous layer was removed quickly due to a precipitate forming in the organic layer. The brown crystalline slurry/solution organic layer was then transferred back to the reaction vessel, some of the solids remaining in the separation funnel were washed into the flask with toluene (50 ml). A dilute solution of sulphuric acid (33.12 g, 0.331 mole) in water (250 ml) was charged to the vessel and agitated for 20 minutes at 50° C. A rapid colour change to yellow occurred in the first minute. After this acid treatment, the contents were again transferred to the separation funnel and the acidic aqueous layer was removed. This was followed by two hot (≈65° C.) water washes (2×200 ml). The organic layer, which had already started to precipitate, was then transferred to a conical flask and placed in an ice bath to complete the precipitation. The solid was filtered off giving a yield of 41.5 g. The filtrates were then rotary evaporated to yield 26.9 g of a yellow solid. Both solids were analysed by G.C. using a standard of known strength to give a combined yield of 57.5% of 3,5-dimethylsalicylaldoxime.

I claim:

1. A method for the preparation of a 2-hydroxyaryldoxime which comprises reacting hydroxylamine or a salt thereof with a 2-hydroxyarylaldehyde, said reaction being performed in the presence of a compound of magnesium, aluminum, titanium, zirconium or chromium and/or under such conditions that the 2-hydroxyarylaldehyde is at least partially in the form of a salt and/or complex of magnesium, aluminum, titanium, zirconium or chromium.

2. A method according to claim 1 wherein the 2-hydroxyarylaldehyde has the formula:

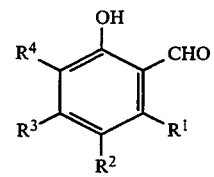

(1)

wherein each of $R^1$, $R^2$, $R^3$ and $R^4$, independently, represents a hydrogen or halogen atom or an alkyl, cycloalkyl, aralkyl, aryl, alkaryl, alkoxy, aryloxy, acyl or hydroxy group.

3. A method according to claim 2 wherein each of the alkyl, cycloalkyl, aralkyl, aryl, alkaryl, alkoxy, aryloxy or acyl groups which may be represented by $R^1$, $R^2$, $R^3$ and $R^4$ contains from 1 to 36 carbon atoms.

4. A method according to claim 2 wherein the 2-hydroxyarylaldehyde has the formula:

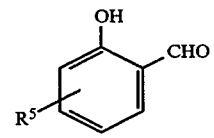

(2)

wherein $R^5$ represents hydrogen or a $C_{1-22}$-alkyl radical.

5. A method according to claim 4 wherein $R^5$ is a $C_{7-12}$-alkyl radical.

6. A method according to claim 2 which comprises reacting hydroxylamine or a salt thereof with a magnesium bis-aryloxide derived from a 2-hydroxyarylaldehyde of Formula 1 as defined in claim 2.

7. A method according to claim 6 wherein the magnesium bis-aryloxide is derived from a 2-hydroxyarylaldehyde of Formula 2:

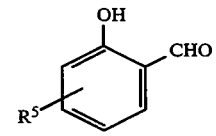

(2)

wherein $R^5$ represents hydrogen or a $C_{1-22}$-alkyl radical.

8. A method according to claim 7 wherein the magnesium bis-aryloxide is magnesium bis-(2-formyl-4-nonylphenoxide).

9. A method according to claim 1 wherein the titanium compound is a titanium (IV) derivative.

10. A method according to claim 1 wherein the 2-hydroxyarylaldehyde used as reactant with the hydroxylamine is itself the direct product of reacting a phenol having at least one free ortho position with formaldehyde or a formaldehyde-liberating compound under substantially anhydrous conditions in the presence of a compound of magnesium, aluminum, titanium, zirconium or chromium and the product thus formed is reacted with the hydroxylamine to form said 2-hydroxyarylaldoxime.

11. A method according to claim 10 wherein hydroxylamine or a hydroxylamine salt is reacted with a magnesium 2-formylphenoxide obtained by reacting a magnesium bis-hydrocarbyloxide derived at least in part from a hydroxyaromatic compound having at least one free position ortho to the hydroxyl group with formaldehyde or a formaldehyde liberating compound under substantially anhydrous conditions.

12. A method according to claim 11 wherein the magnesium 2-formylphenoxide is a magnesium bis(2-formylphenoxide) obtained by reacting a magnesium bis-phenoxide derived from a phenol having at least one free ortho position with formaldehyde or a formaldehyde-liberating compound under substantially anhydrous conditions.

13. A method according to claim 12 wherein the magnesium 2-formylphenoxide is the product of reacting the magnesium bis-hydrocarbyloxide with formaldehyde or a formaldehyde-liberating compound in the presence of a substantially anhydrous solvent system comprising an inert non-polar or low polarity organic solvent and a polar organic solvent.

14. A method according to claim 13 wherein the inert organic solvent comprises an aromatic hydrocarbon or a chlorinated aromatic hydrocarbon.

15. A method according to claim 14 wherein the aromatic hydrocarbon comprises toluene or xylene.

16. A method according to claim 15 wherein the polar organic solvent comprises a polar aprotic solvent or a lower alkanol.

17. A method according to claim 16 wherein the lower alkanol comprises methanol.

18. A method according to claim 11 wherein the magnesium 2-formylphenoxide is the product of reacting the magnesium bis-hydrocarbyloxide with formaldehyde or a formaldehyde-liberating compound at a pressure of from 50 to 700 mm Hg.

19. A method according to claim 11 wherein the magnesium bis-hydrocarbyloxide is a magnesium bis-phenoxide wherein the phenoxide residue may be unsubstituted or may be substituted in any or all of the positions, other than both the 2- and 6- positions, by substituents which do not interfere with the course of the reaction.

20. A method according to claim t0 wherein the magnesium bis-phenoxide is derived-from a phenol of the formula:

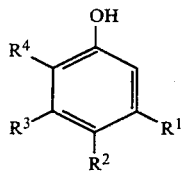

(5)

wherein each of $R^1$, $R^2$, $R^3$ and $R^4$, independently, represents a hydrogen or halogen atom or an alkyl, cycloalkyl, aralkyl, aryl, alkaryl, alkoxy, aryloxy, acyl or hydroxy group.

21. A method according to claim 20 wherein each of the alkyl, cycloalkyl, aralkyl, aryl, alkaryl, alkoxy, aryloxy or acyl groups which may be represented by $R^1$, $R^2$, $R^3$ and $R^4$ contains from 1 to 36 carbon atoms.

22. A method according to claim 20 wherein the magnesium bis-phenoxide is derived from a phenol of the formula:

(6)

wherein $R^5$ represents hydrogen or a $C_{1-22}$-alkyl radical.

23. A method according to claim 22 wherein $R^5$ is a $C_{7-12}$-alkyl radical.

24. A method according to claim 11 wherein the magnesium bis-hydrocarbyloxide is the product of reacting a magnesium alkoxide of the formula:

$$Mg(OR^6)_2 \quad (9)$$

wherein $R^6$ represents an alkyl radical with up to two moles of a phenol having at least one unsubstituted position ortho to the hydroxyl group.

25. A method according to claim 24 wherein the magnesium bis-hydrocarbyloxide is the product of reacting the magnesium alkoxide with from 0.9 to 2 moles of phenol per mole of magnesium alkoxide.

26. A method according to claim 25 wherein the magnesium bis-hydrocarbyloxide is the product of reacting the magnesium alkoxide with from 1.5 to 2 moles of phenol per mole of magnesium alkoxide.

27. A method according to claim 24 wherein $R^6$ is a $C_{1-4}$-alkyl radical.

28. A method according to claim 27 wherein the magnesium alkoxide is magnesium methoxide.

29. A method according to claim 11 wherein the magnesium bis-hydrocarbyloxide is magnesium bis-(4-nonylphenoxide).

* * * * *